United States Patent
Tsuji et al.

(10) Patent No.: US 6,982,235 B2
(45) Date of Patent: Jan. 3, 2006

(54) METHOD FOR REGENERATING SOLID CATALYST

(75) Inventors: Junpei Tsuji, Ichihara (JP); Toshikazu Ohmae, Kisarazu (JP)

(73) Assignee: Sumitomo Chemical Company, Limited, Osaka (JP)

( * ) Notice: Subject to any disclaimer, the term of this patent is extended or adjusted under 35 U.S.C. 154(b) by 120 days.

(21) Appl. No.: 10/471,421

(22) PCT Filed: Mar. 7, 2002

(86) PCT No.: PCT/JP02/02102

§ 371 (c)(1),
(2), (4) Date: Sep. 11, 2003

(87) PCT Pub. No.: WO02/072255

PCT Pub. Date: Sep. 19, 2002

(65) Prior Publication Data

US 2004/0082800 A1    Apr. 29, 2004

(30) Foreign Application Priority Data

Mar. 14, 2001 (JP) .............................. 2001-71781

(51) Int. Cl.
*B01J 20/34*    (2006.01)
*B01J 38/56*    (2006.01)

(52) U.S. Cl. .......................................... 502/31; 502/22
(58) Field of Classification Search ................... 502/31, 502/22

See application file for complete search history.

(56) References Cited

U.S. PATENT DOCUMENTS 6,365,761 B1 *   4/2002   Derks et al. ................. 549/529

FOREIGN PATENT DOCUMENTS

| WO | WO 98/28072 A1 | 7/1998 |
| WO | WO 99/01445 A1 | 1/1999 |
| WO | WO 01/12617 A1 | 2/2001 |

* cited by examiner

*Primary Examiner*—Stanley S. Silverman
*Assistant Examiner*—Jonas N. Strickland
(74) *Attorney, Agent, or Firm*—Sughrue Mion, PLLC

(57) ABSTRACT

A process for regenerating a solid catalyst which has been used for producing propylene oxide through an epoxidation reaction of propylene with an organic peroxide in a reactor packed with the solid catalyst, which comprises allowing a liquid to flow through the catalyst packed in the reactor at a temperature not lower than the maximum reaction temperature of the epoxidation reaction.

According to the present invention, a catalyst can be regenerated with extremely high efficiency without taking the catalyst to be regenerated out of the reactor.

4 Claims, No Drawings

METHOD FOR REGENERATING SOLID CATALYST

TECHNICAL FIELD

The present invention relates to a process for regenerating a solid catalyst. More particularly, the present invention relates to a process for very efficiently regenerating a solid catalyst used for producing propylene oxide through epoxidation of propylene with an organic peroxide in a reactor in which the solid catalyst is packed.

BACKGROUND ART

It is publicly known to produce propylene oxide by epoxidation of propylene with an organic peroxide in a reactor in which the solid catalyst is packed. But, the activity of the catalyst deteriorates with time used. The catalyst in which the activity has deteriorated, require recovery of the activity by changing to a new one or regenerating it.

DISCLOSURE OF THE INVENTION

Under such situations, the subject to be solved by the present invention is to provide a process for regenerating a solid catalyst, which permits the regeneration of the catalyst with extremely high efficiency, without the needs for taking the catalyst to be regenerated out of the reactor when the solid catalyst used for producing propylene oxide by epoxidation of propylene with an organic peroxide in the reactor in which the solid catalyst is packed.

Namely, the present invention relates to a process for regenerating a solid catalyst which has been used for producing propylene oxide through an epoxidation reaction of propylene with an organic peroxide in a reactor packed with the solid catalyst, which comprises allowing a liquid to flow through the catalyst packed in the reactor at a temperature not lower than the maximum reaction temperature of the epoxidation reaction.

BEST MODE FOR CARRYING OUT THE INVENTION

In the present invention, the solid catalyst to be regenerated, is a solid catalyst which has been used for producing propylene oxide through epoxidation of propylene with an organic peroxide in a reactor packed with the solid catalyst.

As the solid catalyst, it is preferable to use a titanium-containing silicon oxide solid catalyst, and as these catalysts, so-called Ti-silica catalysts containing Ti chemically bonded to silicon oxide, are preferable. For example, there are illustrated a product in which a Ti compound is supported on silica carrier, a product in which a Ti-compound is mixed with silicon oxide by a co-precipitation method or a sol-gel method, a zeolite compound containing Ti, and the like. As a shape of the solid catalyst, any shape such as powder, granule, particle, mass or the like can be adopted, but, it is preferable to use a catalyst having several hundreds of micron meters to several tens of micron meters in size taking account of separability of a reaction liquid and a pressure loss of a reactor. Further, when a catalyst is primarily powder, it is preferable to use after making it large in size to some extent through molding.

As the organic peroxide to be reacted with propylene, cumene hydroperoxide, ethylbenzene hydroperoxide and t-butyl hydroperoxide can be exemplified.

As the reactor, a slurry-type reactor, a fixed bed reactor and the like can be used. In a case of a large scale operation, it is preferable to use a fixed bed reactor. Further, the reaction can be carried out by a batch process, semi-batch process or continuous process. The epoxidation temperature is usually 0 to 200° C., and preferably 25 to 200° C. The pressure may be a pressure enough to keep a reaction mixture to a liquid state, and it is advantageously 100 to 10,000 kPa in usual.

The regeneration process of the present invention is a regeneration process of a solid catalyst, which comprises allowing to flow a liquid through a catalyst packed in a reactor used for an epoxidation reaction at a temperature of not lower than the maximum reaction temperature in the epoxidation reaction. Namely, the regeneration is carried out without taking the catalyst out of the reactor used for the epoxidation reaction, therefore it is extremely high efficient. The temperature during the regeneration is a temperature not lower than the maximum reaction temperature in the epoxidation reaction, preferably a temperature higher by 5° C. or more than the maximum reaction temperature, further preferably a temperature higher by 10° C. or more than the maximum reaction temperature.

When the temperature during regeneration is lower than the maximum reaction temperature of epoxidation, an effect of regeneration becomes insufficient. Herein, there is a case of elevating gradually the epoxidation temperature for conpensating a deterioration of the activity with time during the reaction, and the maximum reaction temperature means that in that case.

Further, the temperature at regeneration is preferably 300° C. or less from the viewpoint of durability of the catalyst. In addition, herein, the reaction temperature is a temperature of a catalyst layer, and when there is temperature distribution in the catalyst layer, it is a temperature at the lowest part in temperature.

As the liquid to be flown at regeneration, a liquid used in the reaction system is preferable from the viewpoint of prevention of contamination of a product and the system, and the epoxidation reaction liquid, cumene, liquid propylene ant the like can be illustrated, and liquid propylene is the most preferred. Herein, the liquid propylene also includes a super critical fluid of propylene. AS the regeneration process, a liquid may be passed through the catalyst, and as preferable conditions, a LHSV of 0.5 $h^{-1}$ or more and a flow time of 1 hour or more are mentioned.

EXAMPLE

Example 1

5 cc of a silicon oxide catalyst containing 1.3% by weight of Ti (average particle diameter 0.9 mm, molded article) was packed in a reactor, and a cumene solution having a cumene hydroperoxide concentration of 25 to 35% by weight and propylene were allowed to flow to conduct an epoxidation reaction. The reaction was initiated at a LHSV of 18 $h^{-1}$, reaction pressure of 5.5 MPaG and reaction temperature of 80° C., and the temperature was gradually raised with deterioration of the activity. The reaction temperature became 110° C. after 1800 hours. Next, for regeneration operation, the feed of the cumene solution was stopped, then the temperature of the catalyst layer was elevated to 120° C. and only liquid propylene was allowed to flow through the catalyst layer at a rate of 0.3 g/minute for 18 hours. After liquid propylene was flown, the epoxidation reaction was carried out by allowing to flow a 25 weight % cumene hydroperoxide solution and propylene at 110° C., again. The result is shown in Table 1.

Comparative Example 1

An epoxidation reaction was carried out in the same manner as in Example 1 except that, as regeneration operation, the temperature at which only liquid propylene was flown, was 105° C. The result is shown in Table 1.

Example 2

5 cc of a silicon oxide catalyst containing 1.3% by weight of Ti (average particle diameter 0.9 mm, molded article) was packed in a reactor, and a cumene solution having a cumene hydroperoxide concentration of 25 to 35% by weight and propylene were allowed to flow to conduct an epoxidation reaction. A LHSV of 18 h$^{-1}$ and reaction pressure of 5.5 MPaG were adopted, and after the reaction of 1500 hours, the reaction temperature was 110° C. Next, for regeneration operation, the feed of the cumene solution was stopped, then the temperature of the catalyst layer was elevated to 130° C. and only liquid propylene was allowed to flow through the catalyst layer at a rate of 0.7 g/minute for 20 hours. After liquid propylene was flown, the epoxidation reaction was carried out by allowing to flow a 25 weight % cumene hydroperoxide solution and propylene at 110° C., again. The result is shown in Table 1.

TABLE 1

|  | Example 1 | Comparative Example 1 | Example 2 |
|---|---|---|---|
| Maximum temperature in epoxidation ° C. | 110 | 110 | 110 |
| Regeneration temperature ° C. | 120 | 105 | 130 |

TABLE 1-continued

|  | Example 1 | Comparative Example 1 | Example 2 |
|---|---|---|---|
| CMHP conversion *1% | | | |
| Before regeneration | 54.8 | 54.8 | 42.4 |
| After regeneration | 60.8 | 54.8 | 73.9 |

*1: CMHP; Cumene hydroperoxide: CMHP conversion = converted CMHP(mol)/feed CMHP (mol) × 100

INDUSTRIAL APPLICABILITY

As described above, according to the present invention, there can be provided a process for regenerating a solid catalyst, which permits the regeneration of the catalyst with extremely high efficiency, without the needs for taking the catalyst to be regenerated out of the reactor when the solid catalyst used for producing propylene oxide by epoxidation of propylene with an organic peroxide in the reactor in which the solid catalyst is packed, is regenerated.

What is claimed is:

1. A process for regenerating a solid catalyst which has been used for producing propylene oxide through an epoxidation reaction of propylene with an organic peroxide in a reactor packed with the solid catalyst, which comprises allowing a liquid propylene to flow through the catalyst packed in the reactor at a temperature higher by 5° C. or more than the maximum reaction temperature of the epoxidation reaction.

2. The process according to claim 1, wherein the temperature at which the liquid is flown, is higher by 10° C. or more than the maximum temperature in the epoxidation reaction.

3. The process according to claim 1, wherein the catalyst is a titanium-containing silicon oxide solid catalyst.

4. The process according to claim 1, wherein the organic peroxide is cumene hydroperoxide.

* * * * *